United States Patent
Nakaminami et al.

(10) Patent No.: US 6,740,215 B1
(45) Date of Patent: May 25, 2004

(54) BIOSENSOR

(75) Inventors: Takahiro Nakaminami, Kyoto (JP); Motokazu Watanabe, Katano (JP); Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 226 days.

(21) Appl. No.: 09/959,571

(22) PCT Filed: Nov. 16, 2000

(86) PCT No.: PCT/JP00/08101
§ 371 (c)(1), (2), (4) Date: Oct. 30, 2001

(87) PCT Pub. No.: WO01/36955
PCT Pub. Date: May 25, 2001

(30) Foreign Application Priority Data

Nov. 16, 1999 (JP) ............................. 11/326097

(51) Int. Cl.$^7$ ............................................ G01N 27/327
(52) U.S. Cl. ............................. 204/403.14; 204/403.12
(58) Field of Search .................................... 204/403.14

(56) References Cited

U.S. PATENT DOCUMENTS

| | | | | |
|---|---|---|---|---|
| 4,458,686 A | * | 7/1984 | Clark, Jr. ................... | 600/358 |
| 5,082,786 A | | 1/1992 | Nakamoto .................. | 257/253 |
| 5,298,144 A | * | 3/1994 | Spokane .................... | 204/403.1 |
| 5,512,159 A | * | 4/1996 | Yoshioka et al. ........... | 204/403.08 |

FOREIGN PATENT DOCUMENTS

| | | | |
|---|---|---|---|
| EP | 0127958 A2 | * 12/1984 | ......... G01N/33/348 |
| EP | 0 328 380 | 8/1989 | ......... G01N/27/00 |
| EP | 0 368 474 | 5/1990 | ............ C12M/1/40 |
| EP | 0 795 601 | 9/1997 | ............ C12M/1/40 |
| JP | 57-120853 | 7/1982 | |
| JP | 62-277548 | 12/1987 | |
| JP | 64-68650 | 3/1989 | |
| JP | 3-202764 | 9/1991 | |
| JP | 6-138080 | 5/1994 | |
| JP | 10227755 | 8/1998 | ......... G01N/27/327 |

OTHER PUBLICATIONS

Scheller et al. ("Coupled enzyme reactions in enzyme electrodes using sequence, amplification, competition, and antiference principles," Methods in Enzymology (1988), 137 (Immobilized Enzymes Cells, Pt. D), 29–43).*

"Enzymatically Amplified Voltmmetric Sensor for Microliter Sample Volumes of Salicylate" XP–002220896, PD: 00–00–1995, p. 1896–1902 Moore et al. Analytical Chemistry, vol. 67, No. 11, Jun. 1, 1995.

"Fundamentals of Organic Chemistry", Toshio GOTO, Tokyo Kagaku Dozin Co., Ltd., 1987, pp. 221, 227 and 228, corresponding to "Fundamentals of Organic Chemistry", R.S. Monson, J.C. Shelton, McGraw–Hill Inc.

* cited by examiner

*Primary Examiner*—Alex Noguerola
(74) *Attorney, Agent, or Firm*—McDermott, Will & Emery

(57) ABSTRACT

A biosensor comprising an electrically insulating base plate, an electrode system containing a working electrode and a counter electrode disposed on the base plate, and a reagent system comprising at least an oxidoreductase, a hydrophilic polymer and an electron mediator, wherein the reagent system further comprises a substance having a function to convert an organic product generated by direct reaction of a substrate to be measured with the oxidoreductase to another compound.

18 Claims, 2 Drawing Sheets

BIOSENSOR

TECHNICAL FIELD

The present invention relates to a biosensor for facilitating rapid and highly accurate quantification of a substrate such as glucose contained in a sample.

BACKGROUND ART

With the aim of realizing simple quantification of body fluid components by ordinary people, various types of biosensors have recently been developed which utilize a specific catalytic action of enzymes.

In the following, a method of glucose quantification will be explained as an example of the method of quantifying a component contained in a sample solution. As an electrochemical method of glucose quantification, a method using a combination of glucose oxidase (hereinafter abbreviated to GOD) with an oxygen electrode or a hydrogen peroxide electrode is generally well-known.

GOD selectively oxidizes β-D-glucose as a substrate to D-glucono-δ-lactone using oxygen as an electron mediator. In the presence of oxygen, oxygen is reduced to hydrogen peroxide during the oxidation reaction process by GOD. The decreased volume of oxygen is measured by the oxygen electrode, or the increased volume of hydrogen peroxide is measured by the hydrogen peroxide electrode. The decreased volume of oxygen and the increased volume of hydrogen peroxide are proportional to the content of glucose in the sample solution, so that the quantification of glucose is possible based on the decreased volume of oxygen or the increased volume of hydrogen peroxide.

Glucose sensors of new type have been developed which use as the electron mediator an organic compound or a metal complex such as potassium ferricyanide, a ferrocene derivative and a quinone derivative without using oxygen as the electron mediator. The sensors of this type oxidize the reductant of electron mediator resulting from the enzyme reaction on an electrode, whereby the concentration of glucose contained in the sample solution can be determined based on the amount of the oxidation current. In the case of using such an organic compound or metal complex as the electron mediator in place of oxygen, it is possible to form a reagent layer while the electron mediator is carried in a precise amount and in a stable state together with GOD on the electrode. Further, it is also possible to integrate the reagent layer with an electrode system while keeping it in an almost dry state. Disposable glucose sensors developed based on these technologies have recently been receiving a lot of attention. A typical example thereof is a biosensor disclosed in Japanese Patent Publication No. 2517153. In such a disposable glucose sensor, it is possible to measure the glucose concentration easily with a measurement device by simply introducing the sample solution into the sensor connected detachably to the measurement device.

In the measuring method using the above-described glucose sensor, by a response current of 1 to 10 $\mu A/cm^2$ order, the glucose concentration in the sample can be measured in about 30 seconds. However, it is desired from various fields to develop sensors capable of more rapid glucose quantification with higher sensitivity and accuracy in recent years.

Also, in conventional electrochemical glucose sensors, by the addition of a hydrophilic polymer such as carboxymethyl cellulose to the reagent layer, the measurement results are prevented from being affected by vibrations given to the measurement device from outside. The hydrophilic polymer has another merit that it can function as a binder to immobilize the enzyme on the electrode moderately. The presence of the hydrophilic polymer, however, causes changes in catalytic activity of GOD or thermodynamics of the hydrolytic reaction from D-glucono-δ-lactone to gluconic acid, thereby to cause accumulation of D-glucono-δ-lactone, which is a product of the GOD reaction, in some cases. As a result, the reverse reaction proceeds and the rate of the glucose oxidation reaction decreases, thereby to lower the amount of the reductant of electron mediator generated in a short reaction time, so that the magnitude (sensitivity) of the current of the sensor flowing in response to glucose decreases in some cases. Particularly, trying to obtain a sufficient sensitivity to high concentrations of glucose while securing a good accuracy requires an increase in reaction time in order to generate a large amount of the reductant of electron mediator, so that the measurement tends to require longer time.

DISCLOSURE OF INVENTION

The present invention relates to a biosensor comprising an electrically insulating base plate, an electrode system containing a working electrode and a counter electrode disposed on the base plate, and a reagent system comprising at least an oxidoreductase, a hydrophilic polymer and an electron mediator, wherein the reagent system further comprises a substance having a function to convert an organic product generated by direct reaction of a substrate to be measured with the oxidoreductase to another compound.

The present invention provides a biosensor comprising an electrically insulating base plate, an electrode system containing a working electrode and a counter electrode disposed on the base plate, a cover member disposed over the base plate to form a sample solution supply pathway to the electrode system between the cover member and the base plate, and a reagent system provided to a portion exposed to the sample solution supply pathway, wherein the reagent system comprises at least an oxidoreductase, a hydrophilic polymer, an electron mediator, and a substance having a function to convert an organic product generated by direct reaction of a substrate to be measured with the oxidoreductase to another compound.

BEST MODE FOR CARRYING OUT THE INVENTION

Figure 1:
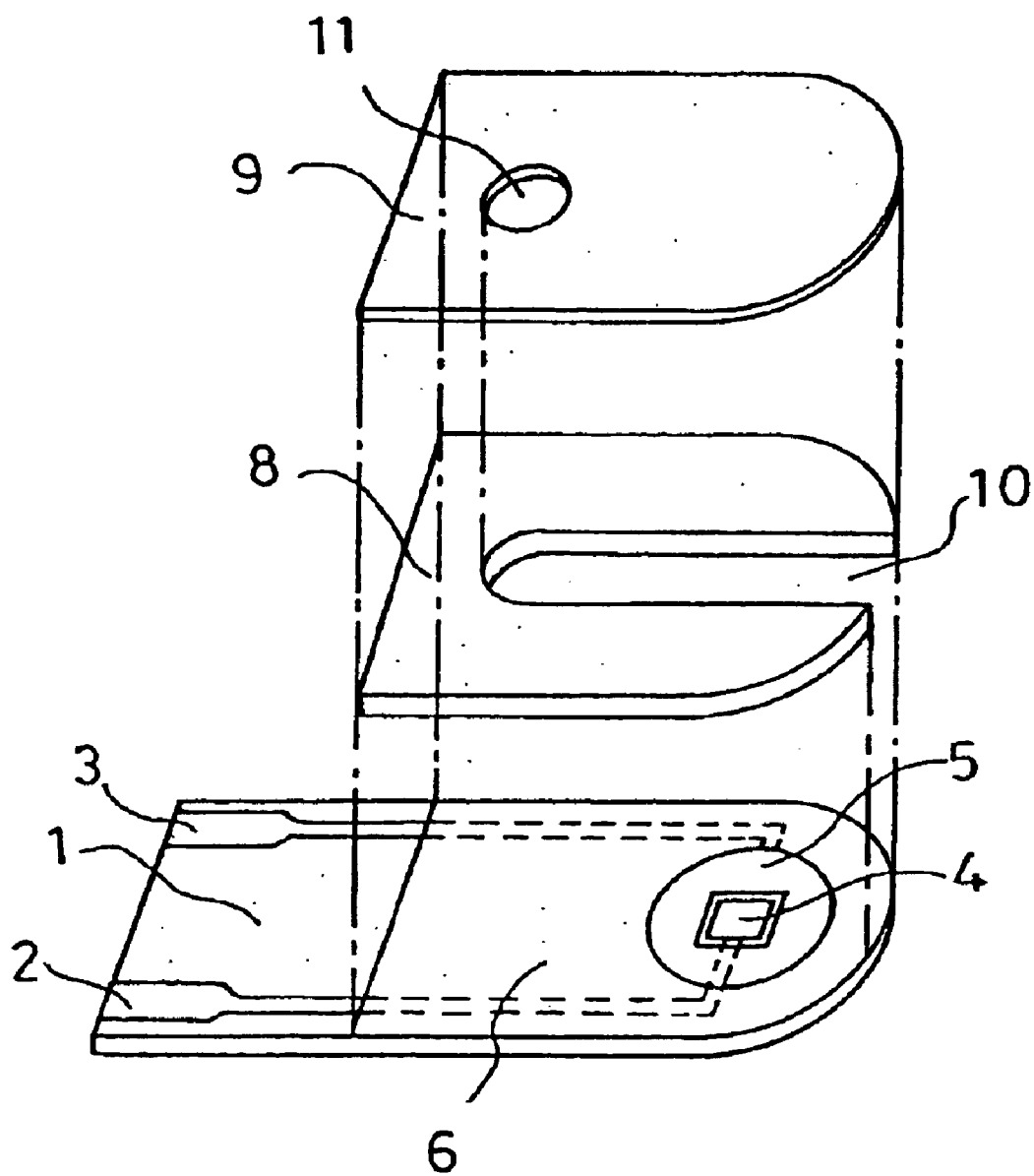
FIG. 1 is an exploded perspective view of a glucose sensor in accordance with one example of the present invention from which the reagent system is omitted.

As described above, a biosensor in accordance with the present invention comprises an electrode system containing a working electrode and a counter electrode disposed on an electrically insulating base plate and a reagent system comprising at least an oxidoreductase, a hydrophilic polymer and an electron mediator, wherein the reagent system further comprises a substance having a function to convert an organic product generated by direct reaction of a substrate to be measured with the oxidoreductase to another compound.

The organic product in an enzyme reaction system is reduced or removed by the substance having a function to convert the organic product to another compound; as a result, the enzyme reaction between the substrate to be measured and the oxidoreductase is allowed to proceed smoothly. This enables rapid and highly accurate measurement of the substrate. As a matter of course, the substance having a function to convert the organic product to another compound must not be one which converts the organic product back to the original substrate or converts it to a compound which would affect the enzyme reaction adversely. Also, the substance must not be one which itself affects the enzyme reaction adversely.

In a preferred mode of the present invention, the organic product generated by direct reaction of the substrate to be measured with the oxidoreductase is an oxidation product generated by oxidation of the substrate by the oxidoreductase, and the concentration of the substrate is obtained on the basis of the current oxidizing the electron mediator that is reduced in conjunction with the enzyme reaction.

In this mode, when the substrate to be measured is D-glucose, β-D-glucose oxidase (EC 1.1.3.4) and glucono-δ-lactonase (EC 3.1.1.17, hereinafter referred to as GLN) are used as the oxidoreductase and the substance having a function to convert the organic oxidation product, D-glucono-δ-lactone, to another compound, respectively. When the oxidoreductase is pyrrolo-quinoline quinone (hereinafter referred to as PQQ) dependent glucose dehydrogenase (EC 1.1.99.17), GLN is used as the substance having a function to convert the oxidation product, D-glucono-δ-lactone, to another compound.

When the oxidoreductase is nicotinamide adenine dinucleotide (hereinafter referred to as NAD) or nicotinamide adenine dinucleotide phosphoric acid (hereinafter referred to as NADP) dependent glucose dehydrogenase (EC 1.1.1.47) (EC 1.1.1.118) (EC 1.1.1.119), GLN is used as the substance having a function to convert the organic oxidation product, D-glucono-δ-lactone, to another compound.

When the oxidoreductase is lactate oxidase, pyruvate oxidase can be used as the substance having a function to convert the oxidation product, pyruvic acid, to other compounds, acetyl phosphate and carbon dioxide.

In the following examples, GLN, which is an enzyme, was used as the substance having a function to convert the product to another compound, but a bioreagent such as an enzyme is not necessarily used. For example, when the substrate to be measured is primary alcohol and the oxidoreductase is alcohol oxidase or alcohol dehydrogenase, it is possible to use hydrazine or an organic compound having an amino residue, which quickly bonds to the oxidation product aldehyde, as the substance having a function to convert it to another compound.

In another mode of the present invention, the organic product generated by direct reaction of the substrate to be measured with the oxidoreductase is a reduction product generated by reduction of the substrate by the oxidoreductase, and the concentration of the substrate is obtained on the basis of the reduction current of the electron mediator that is oxidized in conjunction with the enzyme reaction. In this mode, when the substrate to be measured is glutathione disulfide and the oxidoreductase is glutathione reductase (EC 1.6.4.2), a substance which reacts thiol-selectively, for example, a maleimide compound, is used as the substance having a function to convert an organic product glutathione to another compound.

As the oxidoreductase used in the present invention, an adequate one is selected depending on the substrate contained in the sample solution. Other than the enzymes listed above, it is possible to use, for example, alcohol dehydrogenase, lactate oxidase, cholesterol oxidase, xanthene oxidase, amino acid oxidase, ascorbate oxidase, acyl-CoA oxidase, uricase, glutamate dehydrogenase, or fructose dehydrogenase, as the oxidoreductase.

In order that the substance having a function to convert the organic product generated by reaction of the substrate with the oxidoreductase to another compound could function effectively, a pH buffer is preferably added to the reagent system. In the case of using the pH buffer, there is a need also to consider suitable pH of the oxidoreductase. As the pH buffer, it is possible to use, for example, a buffer containing one or more kinds of phosphate, acetate, borate, citrate, phthalate and glycine, other than the buffer comprising a combination of phosphates used in the examples which will be described later. It is also possible to use one or more kinds of hydrogen salts of the above-listed salts, if existing. Also, it is possible to use a reagent used in the so-called "GOODS buffers". These pH buffers may be contained in the sensor system in the form that is variable according to the structure of the sensor, and the form may be a solid matter or a solution. Further, the buffered pH value realized by the buffer is basically selected for improving the efficiency of the substance having a function to convert the organic product generated by reaction of the substrate with the oxidoreductase to another compound, but the selection should be made in consideration of the balance between that and the influence of the pH buffer on other sensor reactions.

Examples of the electron mediator include potassium ferricyanide, metal complexes such as osmium-tris (bipyridinium) or ferrocene derivatives, quinone derivatives such as p-benzoquinone, phenazinium derivatives such as phenazine methosulfate, phenothiazinium derivatives such as methylene blue, nicotinamide adenine dinucleotide and nicotinamide adenine dinucleotide phosphoric acid. These electron mediators may be in the form of bonding to the polymer backbone or in the form that a part or the whole thereof forms the polymer chain. Further, also when oxygen is used as the electron mediator, a current response can be obtained. These electron mediators are used singly or in combination of two or more.

As the hydrophilic polymer, it is possible to use water-soluble cellulose derivatives, particularly ethyl cellulose, hydroxyethyl cellulose and carboxymethyl cellulose, polyvinyl pyrrolidone, polyvinyl alcohol, gelatin, polyacrylic acid and its salts, starch and its derivatives, a polymer of maleic anhydride or its salts, polyacrylamide, methacrylate resin, poly-2-hydroxyethyl methacrylate and the like.

In the following, the structure of a sensor in accordance with the present invention will be described with reference to FIG. 1 and FIG. 2, but the present invention is not to be limited to only these.

FIG. 1 is an exploded perspective view of a glucose sensor in accordance with the present invention from which the reagent system is removed. A silver paste is printed on an electrically insulating base plate 1 made of polyethylene terephthalate by screen printing to form leads 2 and 3 and the base of later-described electrodes. Next, a conductive carbon paste containing a resin binder is printed on the base plate 1 to form a working electrode 4. This working electrode 4 is in contact with the lead 2. Further, an insulating paste is printed on the base plate 1 to form an insulating layer 6. The insulating layer 6 covers the outer peripheral portion of the working electrode 4, thereby to keep the area of exposed portion of the working electrode 4 constant. Then, a conductive carbon paste containing a resin binder is printed on the base plate 1 so as to be in contact with the lead 3, which forms a ring-like counter electrode 5.

After the above-described electrically insulating base plate 1 is provided with a reagent system in a manner as described later, a spacer 8 having a slit 10 and a cover 9 having an air vent 11 are bonded thereto in a positional relationship as shown by the dashed lines in FIG. 1, thereby to fabricate a biosensor. A sample solution supply pathway is formed in the portion of the slit 10 of the spacer 8. The open end of the slit 10, which is at an end of the sensor, serves as a sample supply port to the sample solution supply pathway.

Figure 2:
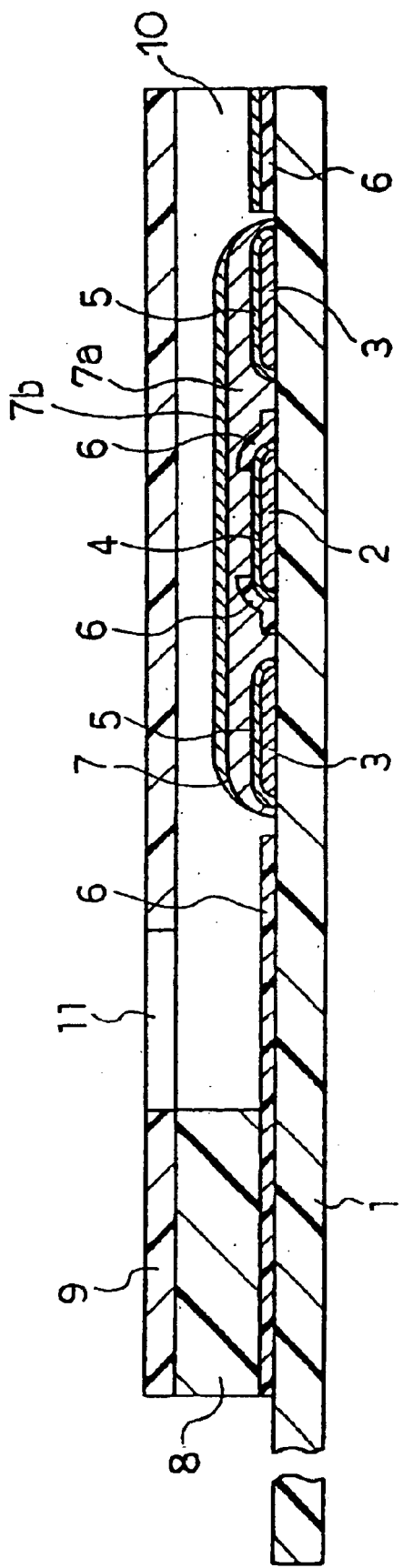
FIG. 2 is a longitudinal cross-sectional view of a vital part of the same glucose sensor.

FIG. 2 is a longitudinal cross-sectional view of the biosensor in accordance with the present invention. A reagent system 7 containing an enzyme and an electron mediator is formed on the base plate 1 on which the electrode system is formed. The reagent system 7 is formed over the electrode system so as to come in contact with the working electrode 4 or the counter electrode 5. This substantially increases the amount of the electron mediator supplied to electrochemical reactions at the electrodes, so that it is possible to obtain a larger response. The reagent system 7, in the example as shown in the figure, is composed of a hydrophilic polymer layer 7a and a layer 7b that is formed thereon and contains GOD, GLN and the electron mediator potassium ferricyanide.

When a sample solution is brought into contact with the open end of the slit 10 forming the sample solution supply pathway of the sensor with the structure as shown in FIG. 2, the sample solution is introduced into the sample solution supply pathway because of capillary phenomenon, thereby to dissolve the reagent system 7, so that the enzyme reaction proceeds. In this way, when the sample solution supply pathway is formed by integrating a cover member composed of the spacer 8 and the cover 9 to the base plate 1 on which the electrode system is provided, the amount of the sample solution containing the substrate to be measured supplied to the sensor can be made constant, so that it is possible to raise the accuracy of the measurement.

In the sensor provided with the sample solution supply pathway as described above, the reagent system may be formed on a portion exposed to the sample solution supply pathway as well as on the electrode system such that the reagent system could dissolve in the sample solution supplied. For example, the reagent system may be formed as follows: the spacer 8 and the cover 9 are bonded to each other, this is turned upside down to form a concave in the slit 10, and a solution for forming the reagent system is dropped in the concave and dried. Alternatively, the reagent system may be divided into plural layers, one on the base plate and another on the cover member side. In this case, each divided layer does not necessarily contain all the reagents. For example, each of the oxidoreductase, the electron mediator and the pH buffer may be contained in a different layer.

The sensor may also be configured only with the base plate 1 without forming the sample solution supply pathway as described above. In this case, the reagent system is formed on or in the vicinity of the electrode system.

In the sensors of any structures, it is preferable to form a hydrophilic polymer layer on the electrode system in order to prevent adsorption of protein to the electrode system or the like.

EXAMPLE 1

An aqueous solution of sodium salt of carboxymethyl cellulose (hereinafter referred to as CMC) was dropped over the electrode system disposed on the base plate 1 and dried to form a CMC layer 7a. An aqueous solution dissolving GOD, GLN and potassium ferricyanide was dropped over the CMC layer 7a and dried to form a layer 7b. The ratio of the activity unit number of GOD to GLN, contained in the reagent system 7 thus formed, was made GOD:GLN=1:2. The amount of GOD was made 1 unit.

A sensor as shown in FIG. 2 was produced by combining the spacer 8 and the cover 9 with the above-described base plate.

An aqueous solution containing a certain amount of D-glucose was supplied to the opening of the sample solution supply pathway of the sensor, that is, the open end of the slit 10 of the spacer. After a lapse of predetermined reaction time, a voltage of 500 mV was applied to the working electrode 4 with respect to the counter electrode 5, and the current value flowing at this time was measured. While D-glucose is oxidized to D-glucono-δ-lactone by the action of GOD, ferricyanide ions are reduced to ferrocyanide ions. The concentration of the ferrocyanide ions thus generated is proportional to the concentration of glucose. Therefore, based on the oxidation current thereof, the concentration of glucose can be measured. D-glucono-δ-lactone generated at this time is decomposed by the action of GLN.

The response current obtained in a reaction time of 5 seconds was plotted against the D-glucose concentration of the solution used; as a result, a favorable linear relationship was observed between the both. The responses obtained when the glucose concentrations were 602 mg/dL and 200 mg/dL were about 500 mV and 190 mV, respectively. Also, for comparison, a sensor not containing GLN in the layer 7b was produced and the responses were measured in the same manner as above: the responses obtained when the glucose concentrations were 602 mg/dL and 200 mg/dL were about 425 mV and 165 mV, respectively. This showed that the responses of the sensor containing GLN in the reagent system were significantly larger than those without GLN. The rates of increase in the responses were 18% and 15%, which were very high values. The reason is considered that the addition of GLN to the reagent system decomposed the product of GOD reaction, D-glucono-δ-lactone, to prevent accumulation thereof in the solution, thereby accelerating the reaction between GOD and glucose.

Also, deserving special note is that the coefficient of response variation (CV) in the sensor to which GLN was added was 75% or lower of that in the sensor without GLN. The addition of GLN improved the accuracy of the measurement.

As described above, the present invention enabled realization of increase in measuring sensitivity. Further, it became clear that the concentration of the substrate to be measured could be quantified accurately and promptly, in a short reaction time of 5 seconds, for example.

When the amount of GOD included in the reagent system was such that the activity became 0.05 to 0.5 unit per 1 square millimeter of sensor system surface area in contact with the sensor system surface, especially favorable results were obtained.

EXAMPLE 2

In the same manner as in Example 1, the CMC layer 7a and the layer 7b containing GOD, GLN and potassium ferricyanide were formed over the electrode system on the base plate 1. This example does not use the spacer 8 and the cover 9.

Over the reagent system 7 of the sensor was dropped an aqueous solution containing a certain amount of D-glucose.

The amount of the D-glucose aqueous solution dropped was made a predetermined amount. After a lapse of predetermined time, a voltage of 500 mV was applied to the working electrode 4 with respect to the counter electrode 5, and the current value flowing at this time was measured. Between the response current obtained and the D-glucose concentration, a favorable linear relationship was observed. Also, the response current obtained was significantly larger than the response current obtained from the sensor not containing GLN in the reagent system 7. In this way, it was found that, even when the sensor did not have the cover member, the above-described effect of GLN enabled realization of the increase in measuring sensitivity.

In Examples 1 and 2, the reagent system 7 was formed so as to come in contact with the electrode system, but even when the reagent system 7 was formed in the vicinity of the sample supply port on the base plate 1 in such a manner that it did not come in contact with the electrode system and was exposed to the sample solution supply pathway, the increase in measuring sensitivity was realized by the addition of GLN. Also, the same effect could be observed also when the reagent system 7 was formed on the cover side so as to be exposed to the sample solution supply pathway.

Further, in the above examples, in order to decompose D-glucono-δ-lactone more effectively, GLN was included in the vicinity of GOD, that is, in the reagent system 7, but GLN may be present at a position different from the reagent system 7 in the sample solution supply pathway of the sensor. If it is at a position in contact with the measuring sample, the addition of GLN increases the measuring sensitivity.

EXAMPLE 3

In this example, a sensor was produced in the same manner as in Example 1, except that a pH buffer composed of a combination of dipotassium hydrogenphosphate ($K_2HPO_4$) and potassium dihydrogenphosphate ($KH_2PO_4$) was added to the layer 7b such that the pH realized by water introduction became 7.

An aqueous solution containing a certain amount of D-glucose was supplied to the opening of the sample solution supply pathway, and after a lapse of predetermined time, a voltage of 500 mV was applied to the working electrode 4 with respect to the counter electrode 5 and the current value flowing at this time was measured. The response current obtained was higher than that of the sensor of the Example 1 not containing a pH buffer in the reagent system 7. This result was obtained presumably because, due to the addition of the pH buffer, the pH of the sample solution was maintained at a value at which GLN more effectively decomposed D-glucono-δ-lactone. It is considered that the addition of the pH buffer changed both of the activity of GOD and the activity of GLN. However, since the suitable pHs for GOD and GLN are about 5 and about 7, respectively, the effect of GLN is considered to have been further promoted in pH 7 of this example.

EXAMPLE 4

In this example, a sensor was produced in the same manner as in Example 1, except that PQQ dependent glucose dehydrogenase (hereinafter referred to as PQQ-GDH) was used in place of the enzyme GOD of the layer 7b. The ratio of the activity unit number of GLN to PQQ-GDH was GLN:PQQ-GDH=2:1. The amount of PQQ-GDH used was 2 units.

An aqueous solution containing a certain amount of D-glucose was supplied to the opening of the sample solution supply pathway of the sensor, and after a lapse of predetermined time, a voltage of 500 mV was applied to the working electrode 4 with respect to the counter electrode 5 and the current value flowing at this time was measured. The response current obtained exhibited a favorable linear relationship with respect to the concentration of D-glucose. Also, for comparison, a sensor not containing GLN in the reagent system 7 was produced and the response value was measured in the same manner as above. In each glucose concentration, the response of the sensor containing GLN in the reagent system was significantly larger than that without GLN. Also when PQQ dependent glucose dehydrogenase was used, the addition of GLN to the reagent system produced the effect of increasing the response.

Further, in the same manner as in Example 3, the addition of a pH buffer to the reagent system further increased the response value.

When the above-mentioned PQQ-GDH was in contact with the sensor system surface such that the activity thereof became 0.1 to 1.5 units per 1 square millimeter of sensor system surface area, especially favorable results were obtained.

EXAMPLE 5

In this example, a sensor was produced in the same manner as in Example 4, except that NAD or NADP dependent glucose dehydrogenase (hereinafter referred to as NAD-GDH and NADP-GDH, respectively) was used in place of PQQ-GDH and that thionine was used in place of potassium ferricyanide. The ratio of the activity unit number of GLN to NAD-GDH or NADP-GDH was made NAD (NADP)-GDH:GLN=1:2.

Under the same conditions as those of Example 4, the response current value to the D-glucose concentration was measured; as a result, the response current obtained was almost proportional to the D-glucose concentration. The reaction between GDH and D-glucose generates reductants of NAD and NADP, which donate electrons to thionine, and thionine thus converted transmits the electrons to the electrode; in this way, a current is generated. What is noted here is that the reductants of NAD and NADP are not products of the substrate (not generated by the reaction between the substrate and the enzyme). The response obtained was significantly larger than that of the similar sensor not containing GLN in the reagent system 7. In this way, also when NAD and NADP dependent glucose dehydrogenase were used, the addition of GLN to the reagent system produced the effect of increasing the response.

Examples 1 to 4 described the case where the ratio of the activity unit number of GLN to GOD, PQQ-GDH and NAD(NADP)-GDH was 2, but also when the ratio to each of the oxidoreuctase was 0.5 to 10, GLN produced the effect of increasing the current. Also, when the above-mentioned ratio was 1 to 3, the effect was particularly large, in which further preferable results were obtained.

Also, in the same manner as in Example 3, the use of the pH buffer further increased the response. Further, the pH range in which the response was remarkably increased was pH 4 to 9 when the substance having a function to convert the organic product of the substrate generated by the reaction of the oxidoreductase to another compound was GLN. In such a pH range, the activity of GLN is considered to be high.

In the examples, the voltage applied to the electrode system was 500 mV, but this is not to be construed as limiting. Any voltage at which the electron mediator reduced can be oxidized at the counter electrode may be applied. For reducing the oxidized electron mediator, a voltage appropriate for the reduction thereof may be applied. Also, the method of detecting the current was used as the measuring method, but any output that changes as the electrochemical reaction proceeds may be substantially used as the subject to be detected. For example, the quantity of electric charge passed in a certain time may be detected. Since the quantity of electric charge is an integral value of the current with respect to time, it may be correlated to the concentration of the substrate to be measured.

As to the reaction time, there are no particular limitations. In a short reaction time, the effect of increasing the response according to the present invention is remarkable, but the increase of the response is observed substantially in all the reaction time.

The reagent system or one or more of the reagents contained in the reagent system may be immobilized on the working electrode so as to make the enzyme insolubilized or not eluted, the electron mediator or the hydrophilic polymer. In the case of immobilization, it is preferable to use the covalent bonding method, the cross-linking immobilization method, the adsorption method, or immobilization methods utilizing interaction of coordinate bond or specific bond. Alternatively, they may be mixed into the electrode material.

As the electrode material, the examples described carbon, but this is not to be construed as limiting. As the working electrode material, it is possible to use any electrically conductive materials which are not oxidized or reduced themselves upon the oxidation or reduction of the electron mediator such as platinum, gold and palladium, in addition to carbon. Further, as the counter electrode material, it is possible to use any electrically conductive materials which are used commonly such as gold, silver and platinum, in addition to carbon. In the above examples, the working electrode and the counter electrode were produced by the screen printing method, but the production method thereof is not subject to any limitations. For example, it is possible to use a process including photo lithography, the vapor deposition method, the chemical vapor deposition method or the sputtering method as another electrode production method. In addition to the working electrode and the counter electrode, an electrode having a stable potential may be provided within the sensor system so as to be used as a reference electrode. In this case, the voltage is applied between the reference electrode and the working electrode.

The shape, arrangement and number of the electrode system are not to be limited to those as shown in the above examples. The shape, arrangement and number of the leads and terminals are also not to be limited to those as shown in the above examples. ability

INDUSTRIAL APPLICABILITY

As described above, the present invention provides a biosensor capable of prompt and highly accurate measurement of a substrate.

What is claimed is:
1. A biosensor comprising an electrically insulating base plate, an electrode system containing a working electrode, and a counter electrode disposed on said base plate, and a reagent system comprising at least an oxidoreductase, and an electron mediator, wherein said reagent system further comprises a substance admixed with said oxidoreductase in said reagent system having a function to convert an organic product generated by direct reaction of a substrate to be measured with said oxidoreductase to another compound, which is different from the substrate.

2. The biosensor in accordance with claim 1, wherein said reagent system is provided on or in the vicinity of said electrode system.

3. A biosensor comprising an electrically insulating base plate, an electrode system containing a working electrode and a counter electrode disposed on said base plate, a cover member disposed over said base plate to form a sample solution supply pathway to said electrode system between said cover member and said base plate, and a reagent system a portion of which is exposed to said sample solution supply pathway, wherein said reagent system comprises at least an oxidoreductase, an electron mediator, and a substance admixed with said oxidoreductase in said reagent system having a function to convert an organic product generated by direct reaction of a substrate to be measured with said oxidoreductase to another compound, which is different from the substrate.

4. The biosensor in accordance with claim 3, wherein said reagent system is in contact with said electrode system.

5. The biosensor in accordance with claim 1 or 3, wherein said reagent system further comprises a pH buffer.

6. The biosensor in accordance with claim 1 or 3, wherein said oxidoreductase is β-D-glucose oxidase (EC 1.1.3.4), said organic product is D-glucono-δ-lactone, and said substance having a function to convert to D-glucono-δ-lactone to another compound is glucono-δ-lactonase (EC 3.1.1.17).

7. The biosensor in accordance with claim 6, wherein the ratio of the activity unit number of said glucono-δ-lactonase to the activity unit number of said glucose oxidase is 0.5 to 10.

8. The biosensor in accordance with claim 6, wherein the ratio of the activity unit number of said glucono-δ-lactonase to the activity unit number of said glucose oxidase is 1 to 3.

9. The biosensor in accordance with claim 1 or 3, wherein said oxidoreductase is pyrrolo-quinoline quinone dependent glucose dehydrogenase (EC 1.1.99.17), said organic product is D-glucono-δ-lactone, and said substance having a function to convert D-glucono-δ-lactone to another compound is glucono-δ-lactonase (EC 3.1.1.17).

10. The biosensor in accordance with claim 9, wherein the ratio of the activity unit number of said glucono-δ-lactonase to the activity unit number of said pyrrolo-quinoline quinone dependent glucose dehydrogenase is 0.5 to 10.

11. The biosensor in accordance with claim 9, wherein the ratio of the activity unit number of said glucono-δ-lactonase to the activity unit number of said pyrrolo-quinoline quinone dependent glucose dehydrogenase is 1 to 3.

12. The biosensor in accordance with claim 1 or 3, wherein said oxidoreductase is nicotinamide adenine dinucleotide or nicotinamide adenine dinucleotide phosphoric acid dependent glucose dehydrogenase (EC 1.1.1.47) (EC 1.1.1.118) (EC 1.1.1.119), said organic product is D-glucono-δ-lactone, and said substance having a function to convert D-glucono-δ-lactone to another compound is glucono-δ-lactonase (EC 3.1.1.17).

13. The biosensor in accordance with claim 12, wherein the ratio of the activity unit number of said glucono-δ-lactonase to the activity unit number of said nicotinamide adenine dinucleotide or nicotinamide adenine dinucleotide phosphoric acid dependent glucose dehydrogenase is 0.5 to 10.

14. The biosensor in accordance with claim 12, wherein the ratio of the activity unit number of said glucono-δ-lactonase to the activity unit number of said nicotinamide adenine dinucleotide or nicotinamide adenine dinucleotide phosphoric acid dependent glucose dehydrogenase is 1 to 3.

15. The biosensor in accordance with claim 5, wherein the pH realized by said pH buffer is 4 to 9.

16. The biosensor in accordance with claim 1 or 3, wherein said oxidoreductase is alcohol oxidase or alcohol dehydrogenase, said organic product is aldehyde, and said substance having a function to convert aldehyde to another compound is hydrazine.

17. The biosensor in accordance with claim 1 or 3, wherein said oxidoreductase is alcohol oxidase or alcohol dehydrogenase, said organic product is aldehyde, and said substance having a function to convert aldehyde to another compound is an organic compound having an amino residue.

18. The biosensor in accordance with claim 1 or 3, wherein the reagent system further comprising a hydrophilic polymer.

* * * * *